(12) United States Patent
Shi

(10) Patent No.: US 11,506,735 B2
(45) Date of Patent: Nov. 22, 2022

(54) SYSTEMS AND METHODS FOR MAGNETIC RESONANCE IMAGING

(71) Applicant: SHANGHAI UNITED IMAGING HEALTHCARE CO., LTD., Shanghai (CN)

(72) Inventor: Yuhang Shi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 292 days.

(21) Appl. No.: 16/875,904

(22) Filed: May 15, 2020

(65) Prior Publication Data

US 2021/0088605 A1    Mar. 25, 2021

(30) Foreign Application Priority Data

Sep. 20, 2019  (CN) .......................... 201910892666.5

(51) Int. Cl.
*G01R 33/24*    (2006.01)
*A61B 5/055*    (2006.01)
*G01R 33/32*    (2006.01)

(52) U.S. Cl.
CPC .............. *G01R 33/24* (2013.01); *A61B 5/055* (2013.01); *G01R 33/32* (2013.01)

(58) Field of Classification Search
None
See application file for complete search history.

(56) References Cited

U.S. PATENT DOCUMENTS

| | | | |
|---|---|---|---|
| 2013/0193968 A1* | 8/2013 | Biber | A61B 5/055 324/309 |
| 2020/0182954 A1* | 6/2020 | Shen | G01R 33/56 |
| 2020/0364908 A1* | 11/2020 | Li | G06T 11/003 |
| 2021/0201477 A1* | 7/2021 | Hu | G06T 7/12 |

* cited by examiner

*Primary Examiner* — Rodney E Fuller
(74) *Attorney, Agent, or Firm* — Metis IP LLC

(57) ABSTRACT

A method for magnetic resonance imaging (MRI) may include obtaining a magnetic resonance (MR) image of a subject, wherein the MR image may be acquired based on a first MRI device and include at least one region of interest (ROI) of the subject. The method may also include selecting, based on the MR image and an ROI determination model, a portion of a main magnetic field generated by the first MRI device. The selected portion of the main magnetic field may correspond to the at least one ROI. The method may also include performing a magnetic field homogenization operation on the selected portion of the main magnetic field.

20 Claims, 8 Drawing Sheets

SYSTEMS AND METHODS FOR MAGNETIC RESONANCE IMAGING

CROSS-REFERENCE TO RELATED APPLICATIONS

This application claims priority to Chinese Patent Application No. 201910892666.5 filed on Sep. 20, 2019, the contents of which are hereby incorporated by reference.

TECHNICAL FIELD

The present disclosure generally relates to magnetic resonance imaging (MRI), and in particular, to systems and methods for main magnetic field homogenization.

BACKGROUND

Magnetic resonance imaging (MRI) is a widely used imaging technique which produces images of an object by exploiting a powerful magnetic field and radio frequency (RF) techniques. MRI employs strong magnetic fields, magnetic field gradients, and radio waves to produce images of the anatomy and/or the physiological processes of the object.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

According to a first aspect of the present disclosure, a system for magnetic resonance imaging (MRI) may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain a magnetic resonance (MR) image of a subject, wherein the MR image may be acquired based on a first MRI device and includes at least one region of interest (ROI) of the subject. The one or more processors may select, based on the MR image and an ROI determination model, a portion of a main magnetic field generated by the first MRI device. The selected portion of the main magnetic field may correspond to the at least one ROI. The one or more processors may perform a magnetic field homogenization operation on the selected portion of the main magnetic field.

In some embodiments, to select, based on the MR image and the ROI determination model, a portion of the main magnetic field generated by the first MRI device, the one or more processors may generate, based on the ROI determination model and the MR image, at least one mask image. One of the at least one mask image may correspond to one or more of the at least one ROI. The one or more processors may obtain a magnetic field map of the subject. The magnetic field map may include the at least one ROI. The one or more processors may obtain at least one ROI image by segmenting the at least one ROI from the magnetic field map based on the at least one mask image. The one or more processors may select, based on the at least one ROI image, the portion of the main magnetic field on which the field homogenization operation is performed.

In some embodiments, the ROI determination model may be obtained according to a first training process including: obtaining a plurality of groups of first training samples; and generating the ROI determination model by training a first preliminary model using the plurality of groups of first training samples.

In some embodiments, the generating the ROI determination model by training the first preliminary model using the plurality of groups of first training samples includes: initializing the first preliminary model; generating the ROI determination model by updating the initialized first preliminary model using a first iteration process including a plurality of iterations; and determining the updated model generated in a last iteration of the plurality of iterations of the first iteration process as the ROI determination model. Each of the plurality of iterations may include obtaining one of the plurality of groups of first training samples that includes a first sample input image and at least one corresponding reference mask image relating to at least one reference ROI of the first sample input image; generating at least one intermediate mask image by inputting the first sample input image of the group of first training sample into a first intermediate model, the first intermediate model being the initialized first preliminary model in a first iteration of the plurality of iterations of the first iteration process or a previously updated model generated in a previous iteration in the first iteration process, the intermediate mask image including at least one candidate ROI of the first sample input image; determining a value of a first cost function based on the at least one intermediate mask image and the at least one reference mask image of the group of first training sample; determining whether a first termination condition is satisfied; in response to determining that the first termination condition is not satisfied, generating an updated model by updating the first intermediate model, and initiating a next iteration.

In some embodiments, the value of the first cost function may be determined based on at least one of a difference between a size of the at least one candidate ROI in the at least one intermediate mask image and a size of the at least one reference ROI in the at least one reference mask image, or a difference between a location of the at least one candidate ROI in the at least one intermediate mask image and a location of the at least one reference ROI in the at least one reference mask image.

In some embodiments, the first termination condition may relate to at least one of the value of the first cost function or a count of iterations of the first iteration process that have been performed.

In some embodiments, to generate, based on the ROI determination model and the MR image, the at least one mask image, the one or more processors may preprocess the MR image. The one or more processors may generate the at least one mask image based on the ROI determination model and the preprocessed MR image.

In some embodiments, to preprocess the MR image, the one or more processors may perform a phase unwrapping operation on the MR image.

In some embodiments, to preprocess the MR image, the one or more processors may preprocess the MR image based on a preprocessing model, the preprocessed MR image having a higher image quality than the MR image.

In some embodiments, the image quality may relate to an image resolution.

In some embodiments, the preprocessing model may be obtained according to a second training process including: obtaining a plurality of groups of second training samples; and generating the preprocessing model by training a second preliminary model using the plurality of groups of second training samples.

In some embodiments, the generating the preprocessing model by training the second preliminary model using the plurality of groups of second training samples includes: initializing the second preliminary model; generating the preprocessing model by updating the initialized second preliminary model using a second iteration process including a plurality of iterations; and determining the updated model generated in a last iteration of the plurality of iterations of the second iteration process as the preprocessing model. Each of the plurality of iterations of the second iteration process may include: obtaining one of the plurality of groups of second training samples that includes a second sample input image and a corresponding reference image, the second sample input image having a higher image quality than the corresponding reference image; generating an intermediate image by inputting the second sample input image of the group of first training sample into a second intermediate model, the second intermediate model being the initialized second preliminary model in a first iteration of the plurality of iterations of the second iteration process or a previously updated model generated in a previous iteration in the second iteration process; determining a value of a second cost function based on the intermediate image and the reference image of the group of second training sample; determining whether a second termination condition is satisfied; in response to determining that the second termination condition is not satisfied, generating an updated model by updating the second intermediate model, initiating a next iteration.

In some embodiments, the second sample input image and the corresponding reference image of at least one of the plurality of groups of second training samples may be obtained by scanning a sample subject using a second MRI device.

In some embodiments, the reference image of at least one of the plurality of groups of second training samples is obtained by scanning a sample subject using a third MRI device, and the corresponding second sample input image of the at least one of the plurality of groups of second training samples is obtained by processing the reference image.

In some embodiments, the value of the second cost function may be determined based on at least one of a difference between pixel values of pixels of the intermediate image and pixel values of pixels of the reference image, or a difference between a homogenization degree of the main magnetic field determined based on the intermediate image and a degree threshold.

In some embodiments, the second termination condition may relate to the value of the second cost function, or a count of iterations of the second iteration process that have been performed.

In some embodiments, the preprocessing model may be constructed based on at least one of a U-shape network (U-Net), a generative adversarial network (GAN), or a recurrent generative adversarial network.

In some embodiments, the ROI determination model may be constructed based on a U-shape network (U-Net).

In some embodiments, the magnetic field homogenization operation may be performed on the selected region of the main magnetic field based on at least one homogeneity threshold each of which corresponds to one of the at least one ROI.

According to another aspect of the present disclosure, a method for magnetic resonance imaging (MRI) may include one or more of the following operations. One or more processors may obtain a magnetic resonance (MR) image of a subject, wherein the MR image may be acquired based on a first MRI device and include at least one region of interest (ROI) of the subject. The one or more processors may select, based on the MR image and an ROI determination model, a portion of a main magnetic field generated by the first MRI device. The selected portion of the main magnetic field may correspond to the at least one ROI. The one or more processors may perform a magnetic field homogenization operation on the selected portion of the main magnetic field.

According to yet another aspect of the present disclosure, a system for magnetic resonance imaging (MRI) may include an image obtaining module configured to obtain a magnetic resonance (MR) image of a subject, wherein the MR image may be acquired based on a first MRI device and include at least one region of interest (ROI) of the subject. The system may also include an ROI determination module configured to select, based on the MR image and an ROI determination model, a portion of a main magnetic field generated by the first MRI device. The selected portion of the main magnetic field may correspond to the at least one ROI. The system may also include a homogenization module configured to perform a magnetic field homogenization operation on the selected portion of the main magnetic field.

According to yet another aspect of the present disclosure, a non-transitory computer readable medium may comprise at least one set of instructions. The at least one set of instructions may be executed by one or more processors of a computing device. The one or more processors may obtain a magnetic resonance (MR) image of a subject, wherein the MR image may be acquired based on a first MRI device and include at least one region of interest (ROI) of the subject. The one or more processors may select, based on the MR image and an ROI determination model, a portion of a main magnetic field generated by the first MRI device. The selected portion of the main magnetic field may correspond to the at least one ROI. The one or more processors may perform a magnetic field homogenization operation on the selected portion of the main magnetic field.

According to yet another aspect of the present disclosure, a system for magnetic resonance imaging (MRI) may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain a magnetic resonance (MR) image of a subject, wherein the MR image may include at least one region of interest (ROI) of the subject. The one or more processors may preprocess the MR image based on a preprocessing model. The preprocessed MR image may have a higher image quality than the MR image. The one or more processors may generate at least one mask image based on an ROI determination model and the preprocessed MR image. One of the at least one mask image may correspond to one or more of the at least one ROI. The one or more processors may obtain at least one ROI image based on the at least one mask image.

According to yet another aspect of the present disclosure, a method for magnetic resonance imaging (MRI) may include one or more of the following operations. One or more processors may obtain a magnetic resonance (MR) image of a subject, wherein the MR image may include at least one region of interest (ROI) of the subject. The one or more processors may preprocess the MR image based on a preprocessing model. The preprocessed MR image may have a higher image quality than the MR image. The one or more processors may generate at least one mask image based on an ROI determination model and the preprocessed MR image. One of the at least one mask image may correspond to one or more of the at least one ROI. The one or more processors may obtain at least one ROI image based on the at least one mask image.

According to yet another aspect of the present disclosure, a system for magnetic resonance imaging (MRI) may include an image obtaining module configured to obtain a magnetic resonance (MR) image of a subject, wherein the MR image may include at least one region of interest (ROI) of the subject. The system may also include an ROI determination module configured to preprocess the MR image based on a preprocessing model. The preprocessed MR image may have a higher image quality than the MR image. The ROI determination module may also be configured to generate at least one mask image based on an ROI determination model and the preprocessed MR image. One of the at least one mask image may correspond to one or more of the at least one ROI. The ROI determination module may also be configured to may obtain at least one ROI image based on the at least one mask image.

According to yet another aspect of the present disclosure, a non-transitory computer readable medium may comprise at least one set of instructions. The at least one set of instructions may be executed by one or more processors of a computing device. The one or more processors may obtain a magnetic resonance (MR) image of a subject, wherein the MR image may include at least one region of interest (ROI) of the subject. The one or more processors may preprocess the MR image based on a preprocessing model. The preprocessed MR image may have a higher image quality than the MR image. The one or more processors may generate at least one mask image based on an ROI determination model and the preprocessed MR image. One of the at least one mask image may correspond to one or more of the at least one ROI. The one or more processors may obtain at least one ROI image based on the at least one mask image.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different levels in ascending order. However, the terms may be displaced by another expression if they achieve the same purpose.

Figure 3:
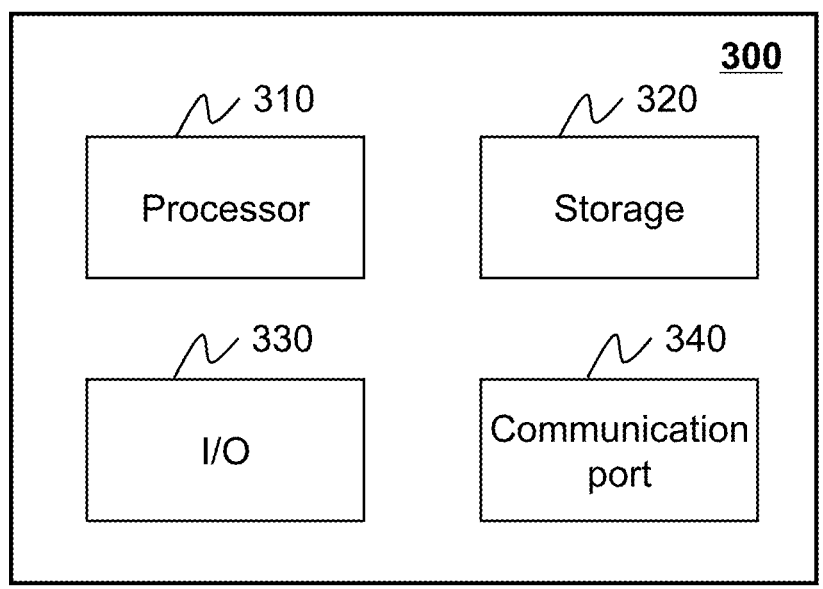
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system. Exemplary MRI systems may include a superconducting magnetic resonance imaging system, a non-superconducting magnetic resonance imaging system, etc. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), image-guided radiotherapy (IGRT), etc. The image-guided radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

MRI scanners typically include a main coil for generating a powerful main magnetic field (called "Bo") which polarizes a subject to be scanned. The image quality depends at least in part on the homogeneity of the main magnetic field. An inhomogeneous main magnetic field may cause distortion in a final magnetic resonance (MR) image, which in some cases may lead to difficulties and/or errors in diagnosis/treatment. Factors leading to inhomogeneous main magnetic field can include internal factors such as production tolerances in the scanner, heating of coils during scanning, vibrations during scanning, or external factors like existence of a ferromagnetic material (e.g., iron) in the vicinity of the scanner (e.g., in a building or room close to where the scanner is located). Therefore, an MRI scanner may include at least one shim coil configured to generate a magnetic field to adjust the homogeneity of the main magnetic field. The magnetic field of the shim coil(s) may be generated by determining an offset electrical current of the shim coil(s). A process for determining the magnetic fields to be generated by the shim coil(s) may take a relatively long time. Therefore, it is desirable to provide systems and/or methods for performing efficient homogenization on the main magnetic field.

An aspect of the present disclosure relates to systems and methods for main magnetic field homogenization in MRI. A magnetic resonance (MR) image of a subject may be obtained by scanning the subject using an MRI scanner. The MR image may include at least one region of interest (ROI) of the subject. The MR image may be preprocessed based on a preprocessing model. The preprocessed MR image may have a higher image quality than the MR image. At least one mask image may be obtained by inputting the preprocessed MR image into an ROI determination model. A magnetic field map of the subject may be obtained. The magnetic field map may include the at least one ROI of the subject. At least one ROI image may be obtained by applying the at least one mask image to the magnetic field map. One or more homogenization parameters configured to generate offset electrical currents which pass through shim coils to generate magnetic fields of the shim coils may be determined by analyzing the at least one ROI image. A homogenization operation may be performed, based on the one or more homogenization parameters, on a portion of a main magnetic field generated by the MRI scanner, so that a homogeneity degree of the portion of the main magnetic field is within a threshold range. The portion of the main magnetic field may correspond to the at least one ROI of the subject.

Comparing to using an image with a relatively high image quality obtained by scanning the subject to determine the at least one mask image, the present disclosure provides a process for determining the at least one mask image based on an MR image with a relatively high image quality that is obtained by processing an MR image with a relatively low image quality using a preprocessing model. The MR image with the relatively low image quality may be obtained by performing a faster scan on the subject. The process for determining the at least one mask image in the present disclosure may improve the accuracy for determining the at least one mask image and efficiency for main magnetic field homogenization.

Additionally or alternatively, by performing the main magnetic field homogenization on only a portion of the main magnetic field corresponding to the at least ROI of the subject, the efficiency of the main magnetic field homogenization may be improved without compromising the image quality of the resultant image.

Figure 1:
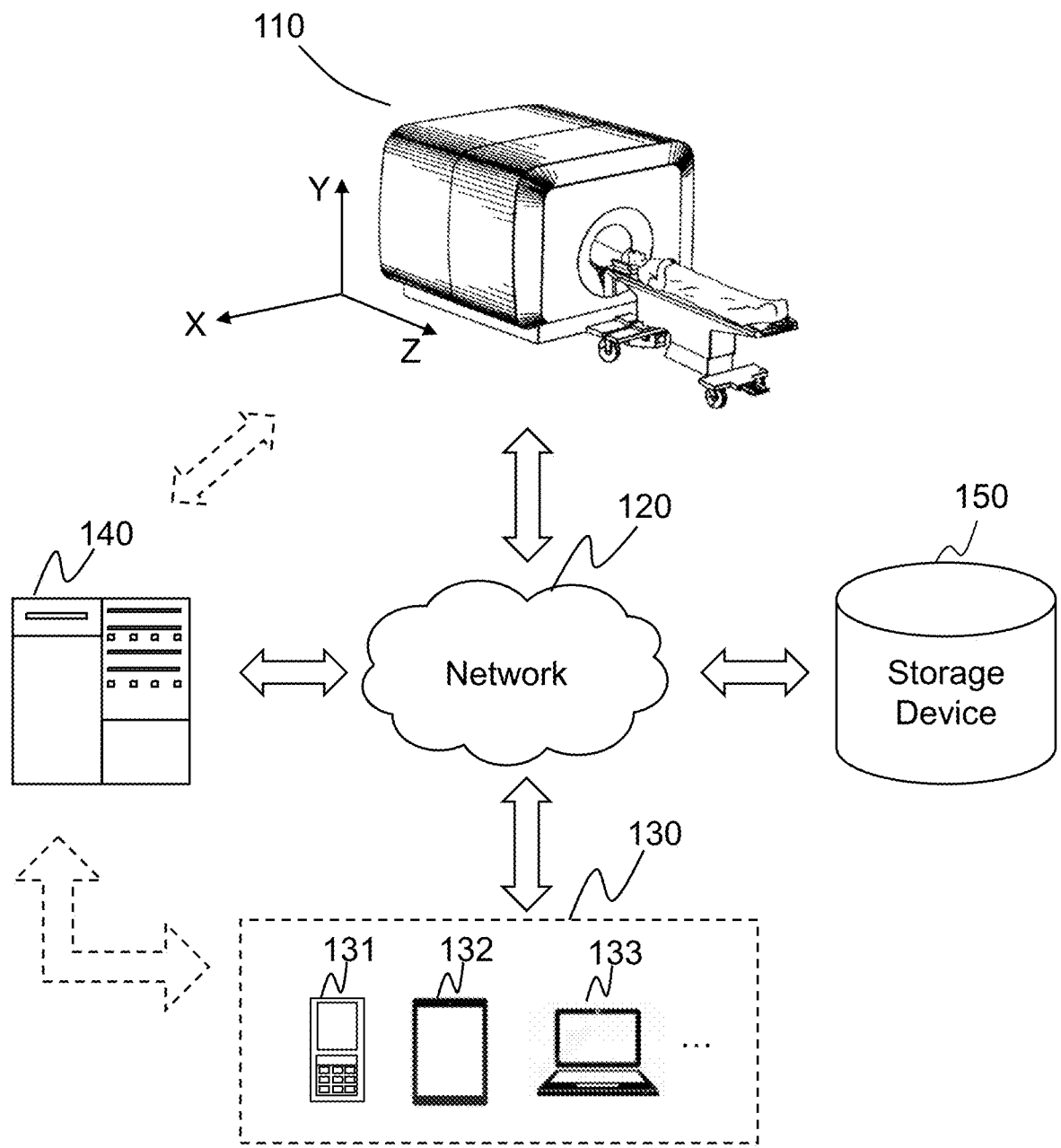
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As illustrated, the MRI system 100 may include a scanner 110, a network 120, a user device 130, a processing device 140, and a storage device 150. The components of the MRI system 100 may be connected in one or more of various ways. Mere by way of example, as illustrated in FIG. 1, the scanner 110 may be connected to the processing device 140 through the network 120. As another example, the scanner 110 may be connected to the processing device 140 directly (as indicated by the bi-directional arrow in dotted lines linking the scanner 110 and the processing device 140). As a further example, the storage device 150 may be connected to the processing device 140 directly or through the network 120. As still a further example, the user device 130 (e.g., 131, 132, 133, etc.) may be connected to the processing device 140 directly (as indicated by the bi-directional arrow in dotted lines linking the user device 130 and the processing device 140) or through the network 120.

The scanner 110 may scan an object located within its detection region and generate a plurality of imaging data relating to the object. In the present disclosure, "subject" and "object" are used interchangeably. Mere by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

In some embodiments, the scanner 110 may include an MRI scanner, a multi-modality device, etc. Exemplary multi-modality device may include an MRI-CT device, a PET-MRI device, etc. In some embodiments, the MRI scanner may be a close-bore scanner or an open-bore scanner. In the present disclosure, the X axis, the Y axis, and the Z axis shown in FIG. 1 may form an orthogonal coordinate system. The X axis and the Z axis shown in FIG. 1 may be horizontal, and the Y axis may be vertical. As illustrated, the positive X direction along the X axis may be from the right side to the left side of the scanner 110 seen from the direction facing the front of the scanner 110; the positive Y direction along the Y axis shown in FIG. 1 may be from the lower part to the upper part of the scanner 110; the positive Z direction along the Z axis shown in FIG. 1 may refer to a direction in which the object is moved out of the scanning channel (or referred to as the bore) of the scanner 110. More description of the scanner 110 may be found elsewhere in the present disclosure. See, e.g., FIG. 2 and the description thereof.

The network 120 may include any suitable network that can facilitate the exchange of information and/or data for the MRI system 100. In some embodiments, one or more components of the MRI system 100 (e.g., the scanner 110, the user device 130, the processing device 140, or the storage device 150) may communicate information and/or data with one or more other components of the MRI system 100 via the network 120. For example, the processing device 140 may obtain magnetic resonance (MR) data (also referred to as MR signals, echo signals, or echo data) from the scanner 110 via the network 120. As another example, the user device 130 and/or the storage device 150 may obtain one or more images from the processing device 140. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the MRI system 100 may be connected to the network 120 to exchange data and/or information.

The user device 130 may include a mobile device 131, a tablet computer 132, a laptop computer 133, a desktop computer (not shown), a workstation (not shown), or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the user device 130 may remotely operate the scanner 110 and/or the processing device 140. In some embodiments, the user device 130 may operate the scanner 110 and/or the processing device 140 via a wireless connection. In some embodiments, the user device 130 may receive information and/or instructions inputted by a user, and send the received information and/or instructions to the scanner 110 or to the processing device 140 via the network 120. For example, a user (e.g., a doctor, a technician, or an engineer, etc.) of the MRI system 100 may set a scan protocol though the user device 130. The user device 130 may send the scan protocol to the processing device 140 to direct the processing device 140 to cause the scanner 110 (e.g., the MRI scanner) to operate according to the scan protocol. In some embodiments, the user device 130 may receive data and/or information from the processing device 140 and/or the storage device 150. For example, the user device 130 may obtain one or more images from the processing device 140 and/or the storage device 150.

The processing device 140 may process data and/or information obtained from the scanner 110, the user device 130, and/or the storage device 150. For example, the processing device 140 may obtain MR data from the scanner 110 and determine one or more images based on the MR data. As another example, the processing device 140 may receive one or more instructions from the user device 130 and cause the scanner 110 to operate according to the one or more instructions. In some embodiments, the processing device 140 may be a single server, or a server group. The server group may be centralized or distributed. In some embodiments, the processing device 140 may be local or remote. For example, the processing device 140 may access information and/or data stored in or acquired by the scanner 110, the user device 130, and/or the storage device 150 via the network 120. As another example, the processing device 140 may be directly connected to the scanner 110 (as illustrated by the bidirectional arrow in dashed lines connecting the processing device 140 and the scanner 110 in FIG. 1), the user device 130 (as illustrated by the bidirectional arrow in dashed lines connecting the processing device 140 and the user device 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300 having one or more components illustrated in FIG. 3 in the present disclosure.

The storage device 150 may store data and/or instructions. In some embodiments, the storage device 150 may include a database, a picture archiving and communication system, a file system, or the like, or any combination thereof. In some embodiments, the storage device 150 may store data obtained from the scanner 110, the user device 130 and/or the processing device 140. For example, the storage device 150 may store MR data acquired by the scanner 110. As another example, the storage device 150 may store medical images (e.g., MR images) generated by the processing device 140 and/or the user device 130. As a further example, the storage device 150 may store preset scan parameters (e.g., preset scan protocols) of the MRI system 100. In some embodiments, the storage device 150 may store data and/or instructions that the processing device 140 may execute or use to perform exemplary methods described in the present disclosure. For example, the storage device 150 may store instructions that the processing device 140 may execute to perform main magnetic field homogenization on a main magnetic field generated by the scanner 110. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the MRI system 100 (e.g., the scanner 110, the processing device 140, the user device 130, etc.). One or more components of the MRI system 100 may access the data or instructions stored in the storage device 150 via the network 120. In some embodiments, the storage device 150 may be directly connected to or communicate with one or more components of the MRI system 100 (e.g., the scanner 110, the processing device 140, the user device 130, etc.). In some embodiments, the storage device 150 may be part of the processing device 140.

In some embodiments, the MRI system 100 may further include one or more power supplies (not shown in FIG. 1) connected to one or more components of the MRI system 100 (e.g., the scanner 110, the processing device 140, the user device 130, the storage device 150, etc.).

Figure 2:
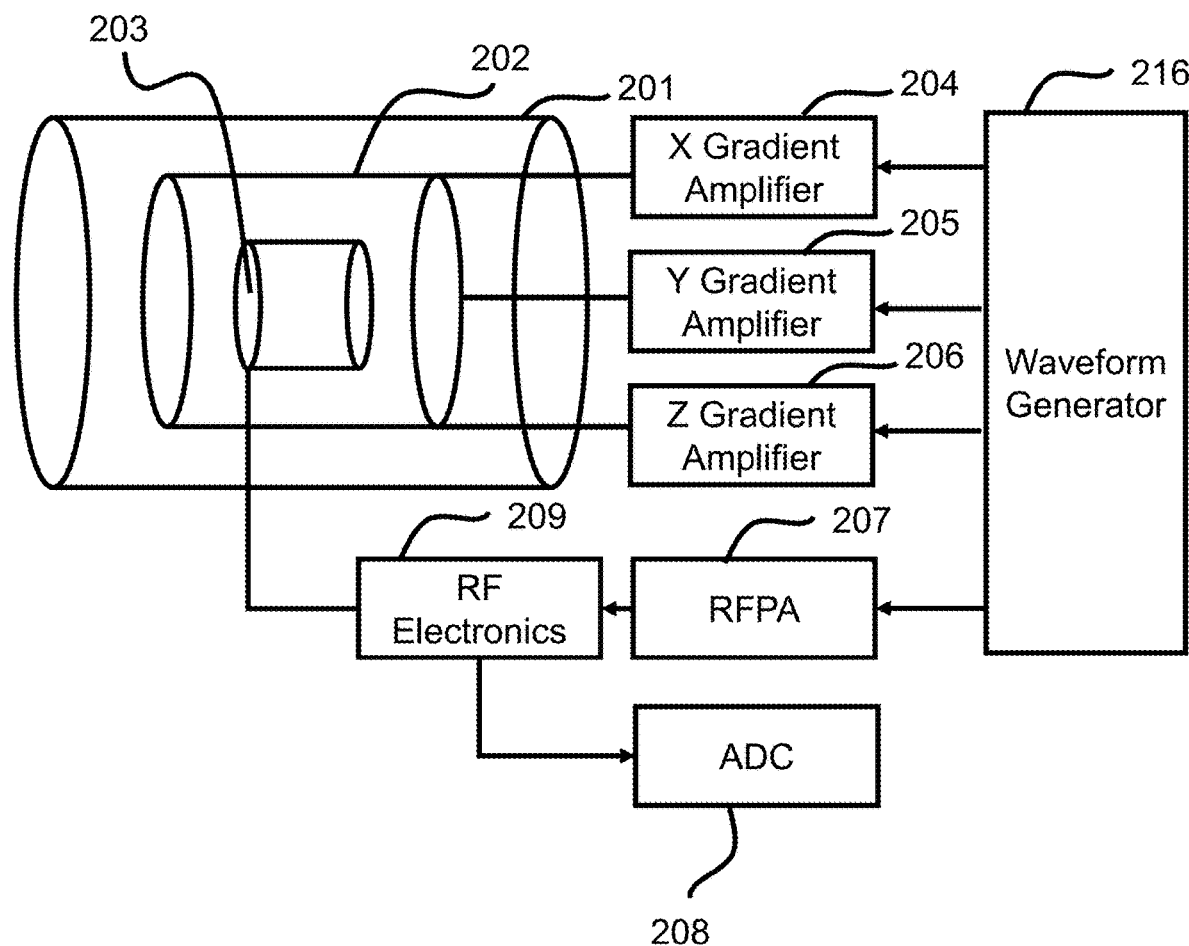
FIG. 2 is a schematic diagram illustrating an exemplary MRI scanner according to some embodiments of the present disclosure.

FIG. 2 is a schematic diagram illustrating an exemplary MRI scanner according to some embodiments of the present disclosure. As illustrated, the main magnet 201 may generate a first magnetic field (or referred to as a main magnetic field) that may be applied to an object (also referred to as a subject) exposed inside the field. The main magnet 201 may include a resistive magnet or a superconductive magnet that both need a power supply (not shown) for operation. Alternatively, the main magnet 201 may include a permanent magnet. The main magnet 201 may include a bore that the object is placed within. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of an object may vary as a function of their positions inside the gradient field, thereby encoding spatial information into MR signals generated by the object being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of MR signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X axis, the Y axis, or the Z axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X axis, the Y axis, the Z axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate MR signals related to the object being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting MR signals (e.g., echoes). After excitation, the MR signals generated by the object may be sensed by the RF coils 203. The receive amplifier then may receive the sensed MR signals from the RF coils 203, amplify the sensed MR signals, and provide the amplified MR signals to the ADC 208. The ADC 208 may transform the MR signals from analog signals to digital signals. The digital MR signals then may be sent to the processing device 140 to be filled into k-space to obtain k-space data.

In some embodiments, the gradient coils 202 and the RF coils 203 may be circumferentially positioned with respect to the object. It is understood by those skilled in the art that the main magnet 201, the gradient coils 202, and the RF coils 203 may be situated in a variety of configurations around the object.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the scanner 110 may further include an object positioning system (not shown). The object positioning system may include an object cradle and a transport device. The object may be placed on the object cradle and be positioned by the transport device within the bore of the main magnet 201.

MRI systems (e.g., the MRI system 100 in the present disclosure) may be commonly used to obtain an interior image from an object (e.g., a patient) for a particular region of interest that can be used for the purposes of, e.g., diagnosis, treatment, or the like, or a combination thereof. MRI systems include a main magnet (e.g., the main magnet 201) assembly for providing a main magnetic field to align the individual magnetic moments of the H atoms within the patient's body. During this process, the H atoms oscillate around their magnetic poles at their characteristic Larmor frequency. If the object is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an MR signal. The MR signal is received and processed to form an MR image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization. In the present disclosure, terms "MR data," "MR signal," "echo," "echo data," and "echo signal" may be used interchangeably.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the X, Y, and Z directions (e.g., same as or similar to the X axis, the Y axis, and the Z axis in FIG. 1), having a particular timing, frequency, and phase, may be superimposed on the magnetic field such that the RF excitation signal excites the H atoms in one or more desired slices of the patient's body, and unique phase and frequency information is encoded in the MR signal depending on the location of the H atoms in the "image slice."

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include spin echo sequences, gradient echo sequences, diffusion sequences, inversion recovery sequences, saturation recovery sequences, or the like, or any combination thereof. For instance, the spin echo sequences may include fast spin echo (FSE), turbo spin echo (TSE), rapid acquisition with relaxation enhancement (RARE), half-Fourier acquisition single-shot turbo spin-echo (HASTE), turbo gradient spin echo (TGSE), or the like, or any combination thereof. The protocol may also include information regarding image contrast and/or ratio, a region of interest (ROI), slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), one or more image reconstruction algorithms, or the like, or any combination thereof.

For an MRI scan, the acquired MR signals (also referred to as MR data) may be digitized and filled into the k-space to obtain the k-space data. One or more images may be generated based on the k-space data in accordance with the MRI imaging protocol that is used.

FIG. 3 is a schematic diagram illustrating exemplary hardware and/or software components of a computing device on which the processing device 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (program code) and perform functions of the processing device 140 in accordance with the techniques described herein. The computer instructions may include routines, programs, objects, components, signals, data structures, procedures, modules, and functions, which perform particular functions described herein. For example, the processor 310 may generate one or more images based on MR data. In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be noted that the computing device 300 in the present disclosure may also include multiple processors, and thus operations of a method that are performed by one processor as described in the present disclosure may also be jointly or separately performed by the multiple processors. For example, if in the present disclosure the processor of the computing device 300 executes both operations A and B, it should be understood that operations A and B may also be performed by two different processors jointly or separately in the computing device 300 (e.g., a first processor executes operation A and a second processor executes operation B, or the first and second processors jointly execute operations A and B).

Merely by way example, the processor 310 may receive instructions to follow an MRI scan protocol for imaging/scanning the object. For example, the processor 310 may instruct the object positioning system of the scanner 110 to move the object to a proper position within the bore of the main magnet 201. As another example, the processor 310 may also provide certain control signals to control the main magnet 201 to generate a main magnet field with a specific strength.

The processor 310 may receive control signals to set the shape, amplitude, and/or timing of the gradient waveforms and/or the RF waveforms, and send the set parameters to the waveform generator 216 to instruct the waveform generator 216 to generate a particular gradient waveform sequence and pulse sequence that are to be applied to the gradient coils 202 and the RF coils 203 through the amplifiers 204-207, respectively.

The processor 310 may also sample data (e.g., echoes) from the RF coils 203 based on one or more sampling parameters including, e.g., timing information (e.g., the length of data acquisition), the type of k-space data acquisition (e.g., undersampling, oversampling, etc.), sampling trajectory (e.g., a Cartesian trajectory, a non-Cartesian trajectory such as spiral trajectory, radial trajectory, etc.), or the like, or a combination thereof. In some embodiments, the timing information may be input by a user (e.g., an operator) or autonomously determined by the MRI system 100 based on one or more other parameters (e.g., clinical needs) of an imaging process. The timing information may correspond to the type of the gradient and RF waveforms that are sent to the gradient coils 202 and the RF coils 203, respectively, so that the MR signals are correctly sampled. The processor 310 may also generate one or more MR images by reconstructing the sampled data (e.g., the k-space data).

The storage 320 may store data/information obtained from the scanner 110, the user device 130, the storage device 150, or any other component of the MRI system 100. In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 140 for generating one or more images based on MR data. In some embodiments, the storage 320 may store one or more reconstructed MR images.

The I/O 330 may input or output signals, data, or information. In some embodiments, the I/O 330 may enable user interaction with the processing device 140. In some embodiments, the I/O 330 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected to a network (e.g., the network 120) to facilitate data communications. The communication port 340 may establish connections between the processing device 140 and the scanner 110, the user device 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
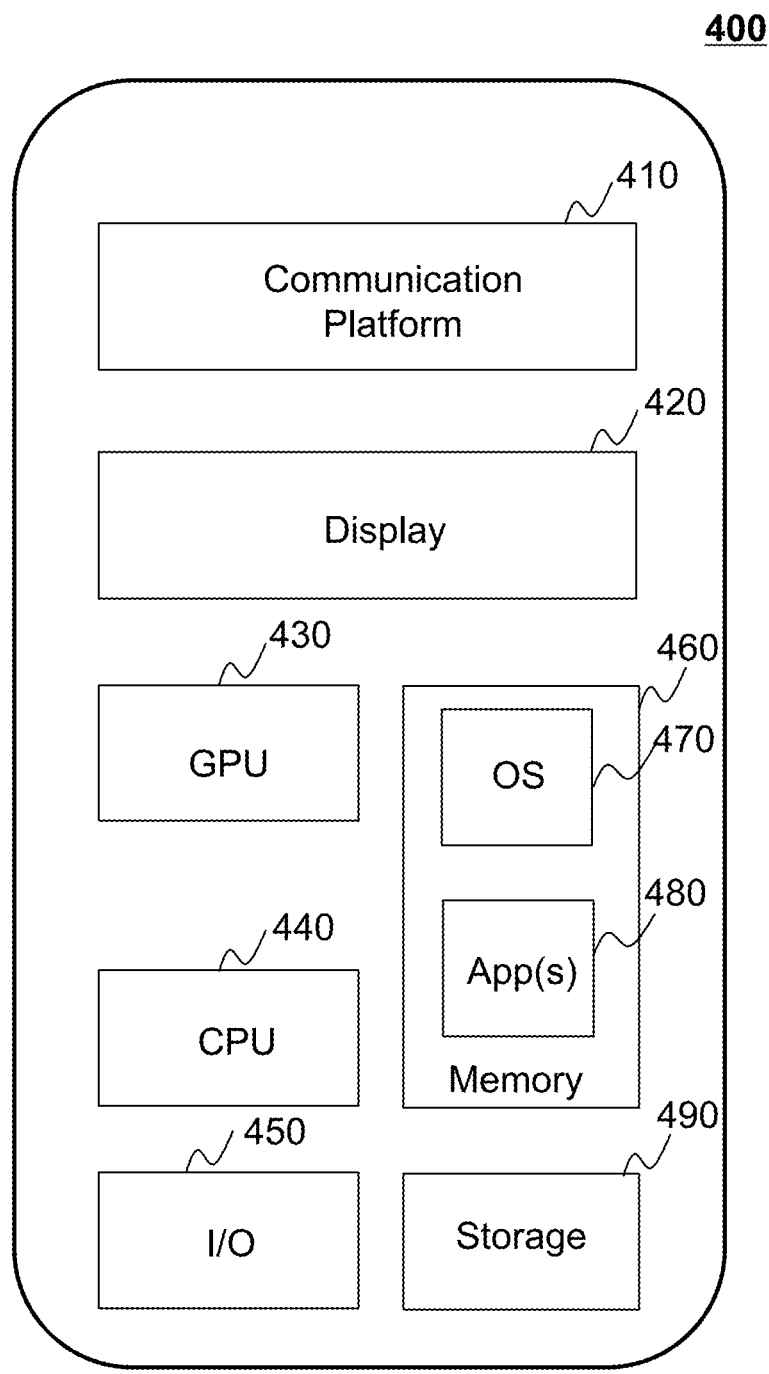
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which the user device 130 may be implemented according to some embodiments of the present disclosure. As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the MRI system 100 via the network 120. Merely by way of example, a user (e.g., a doctor, a technician, an engineer, an operator, etc.) of the MRI system 100 may input data related to an object (e.g., a patient) that is being/to be imaged/scanned through the I/O 450. The data related to the object may include identification information (e.g., the name, age, gender, medical history, contact information, physical examination result, etc.) and/or the test information including the nature of the MRI scan that must be performed. The user may also input parameters needed for the operation of the scanner 110, such as image contrast and/or ratio, a region of interest (ROI), slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with steady-state procession, and so on), a flip angle value, acquisition time (TA), echo time (TE), repetition time (TR), inversion time (TI), saturation time (TS), echo train length (ETL), the number of phases, the number of excitations (NEX), bandwidth (e.g., RF receiver bandwidth, RF transmitter bandwidth, etc.), a scan type, a type of sampling, time points when the MR data is acquired (e.g., cardiac phases, respiratory phases, etc.), time points when an acquisition phase of the scan is triggered, a duration of a period of the acquisition phase, or the like, or any combination thereof. The I/O may also display MR images generated based on the sampled data.

In some embodiments, the I/O 450 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5:
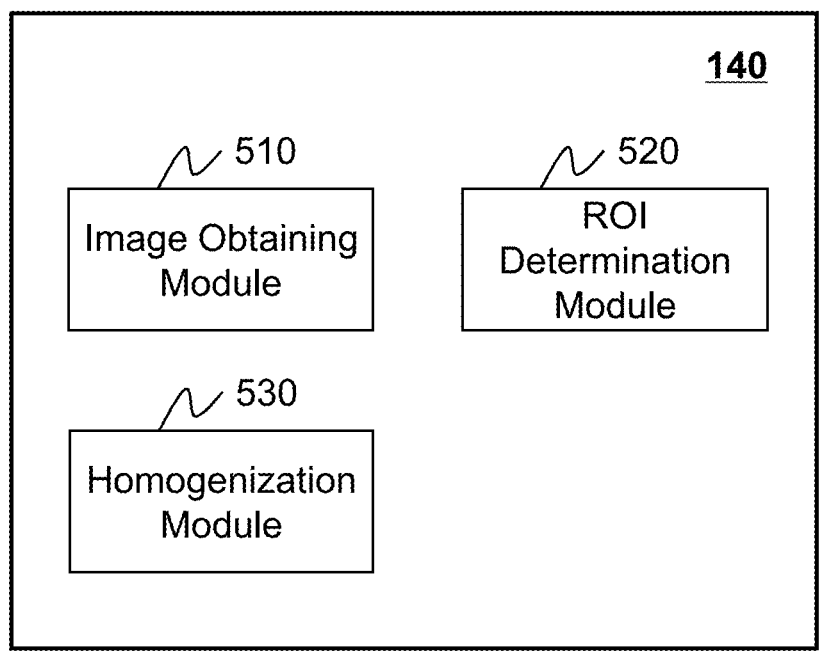
FIG. 5 is a schematic block diagram illustrating an exemplary processing device according to some embodiments of the present disclosure.

FIG. 5 is a schematic block diagram illustrating an exemplary processing device according to some embodiments of the present disclosure. The processing device 140 may include an image obtaining module 510, an ROI determination module 520, and a homogenization module 530.

The image obtaining module 510 may obtain an MR image of a subject. The MR image may be acquired by performing a scan on the subject using the scanner 110 of the MRI system 100 illustrated in FIG. 1. In some embodiments, the MR image may include at least one region of interest (ROI) of the subject. The at least one ROI may include tissue of the subject that a user (e.g., a doctor, an engineer, a technician, etc.) is interested in.

The ROI determination module 520 may select, based on the MR image and an ROI determination model, a portion of a main magnetic field generated by the scanner 110 (e.g., the main magnet 201 in FIG. 2). The selected portion of the main magnetic field may correspond to the at least one ROI.

In some embodiments, the ROI determination module 520 may generate, based on the ROI determination model and the MR image, at least one mask image. In some embodiments, a mask image may be a binary image. As used herein, a binary image may denote that the gray value of a pixel in the binary image may be "1" or "0." In some embodiments, the at least one mask image may indicate the at least one ROI. In some embodiments, each of the at least one mask image may indicate one or more of the at least one ROI. For example, one or more of the at least one ROI of the subject may be represented as pixels with the gray value of 1 in one of the at least one mask image, and the gray values of the rest pixels of the one of the at least one mask image may be equal to 0.

Figure 7:
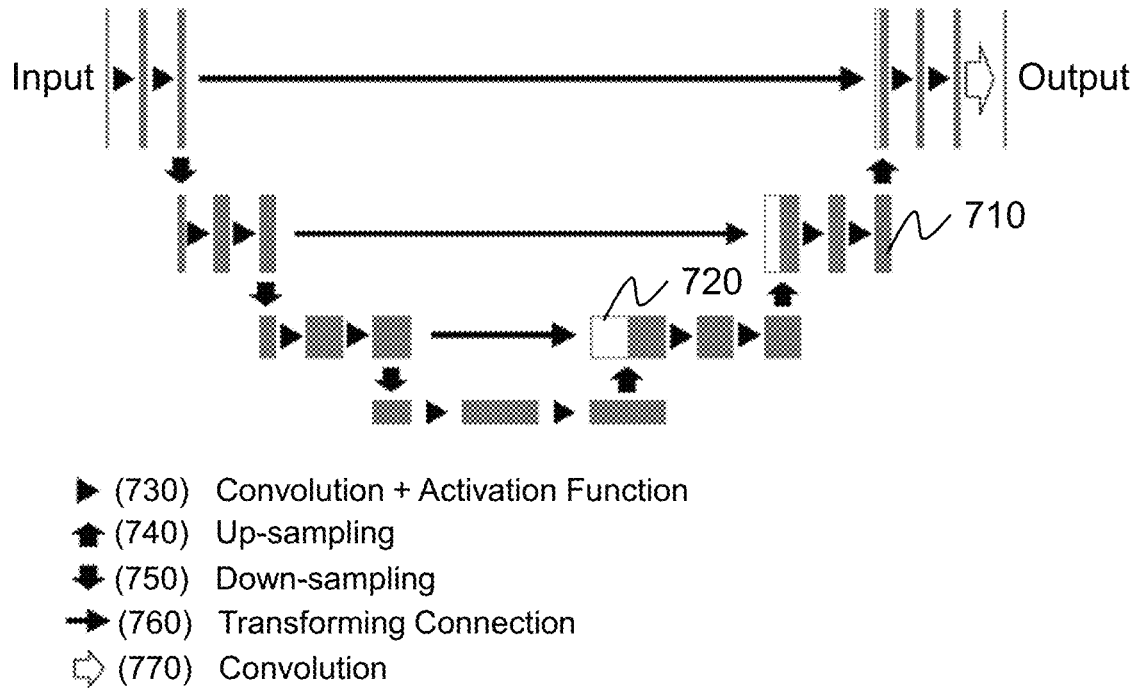
FIG. 7 is a schematic diagram illustrating an exemplary U-shape convolutional neural network (U-Net) architecture according to some embodiments of the present disclosure.
Figure 8:
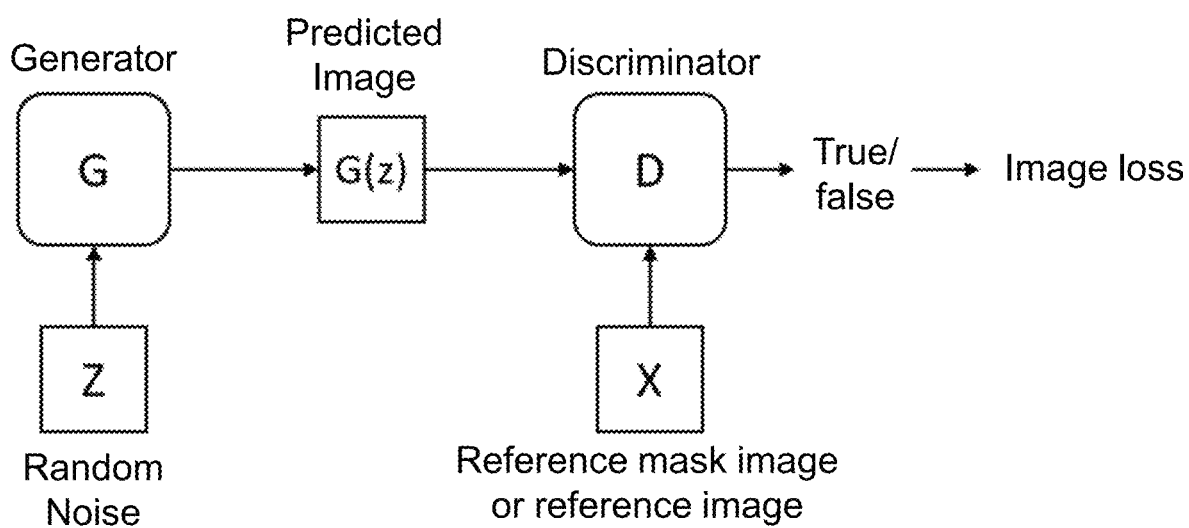
FIG. 8 is a schematic diagram illustrating an exemplary generative adversarial neural network (GAN) architecture according to some embodiments of the present disclosure.

In some embodiments, the ROI determination model may be constructed based on deep learning. In some embodiments, the ROI determination model may be constructed based on a neural network model. In some embodiments, the ROI determination model may be constructed based on a convolutional neural network (CNN), a self-encoding neural network based on multilayer neurons, a deep belief neural network, or the like. Exemplary CNN may include a fully convolutional neural network (FCN), a U-shape convolutional neural network (U-Net) (e.g., as shown in FIG. 7) that is an FCN-based deformation architecture, a generative adversarial neural network (GAN) (e.g., as shown in FIG. 8), a recurrent generative adversarial neural network, or the like. In some embodiments, the training process of the ROI determination model may include a supervised learning process, an unsupervised learning process, a semi-supervised learning process, or an active learning process.

In some embodiments, before generating the at least one mask image, the ROI determination module 520 may perform a preprocessing operation on the MR image. The ROI determination module 520 may generate the at least one mask image based on the ROI determination model and the preprocessed MR image. In some embodiments, the preprocessing operation may include stretching, enlarging, shrinking, cutting, or the like, or any combination thereof.

In some embodiments, since the phase is defined within the range of ($-\pi$, $+\pi$) when a phase image is generated, phase wrapping may occur in the phase image. If the MR image is a phase image, the preprocessing operation may include phase unwrapping. In some embodiments, the ROI determination module 520 may perform phase unwrapping on the MR image based on a path tracking algorithm, a minimum norm algorithm, or the like, or any combination thereof. Exemplary path tracking algorithms may include a branch-cut algorithm.

In some embodiments, if the MR image is of a relatively low image quality, the preprocessing operation may include a process for improving the image quality of the MR image. The preprocessed MR image may have a higher image quality than the MR image. For example, the preprocessed MR image may be regarded as having a higher image quality than the MR image if the image resolution of the preprocessed MR image is higher than that of the MR image. Additionally or alternatively, the preprocessed MR image may be regarded as having a higher image quality than the MR image if the preprocessed MR image has a lower noise level (e.g., fewer artifacts) than the MR image. In some embodiments, the ROI determination module 520 may perform the preprocessing for improving the image quality of the MR image based on interpolation, a machine learning model, or the like, or any combination thereof. For example, the ROI determination module 520 may obtain the preprocessed MR image by processing the MR image based on a preprocessing model.

Compared to the MR image, the at least one ROI in the preprocessed MR image with a higher image quality may be easier to be differentiated from each other. Using the preprocessed MR image with a higher image quality to determine the at least one mask image may improve the accuracy for determining the at least one mask image. A process for obtaining an image with a relatively high image quality by scanning the subject may take a longer time than a process for obtaining an image with a relatively low image quality by scanning the subject. The preprocessed MR image with a higher image quality may be obtained by processing an MR image with a lower image quality, instead of by performing a high quality scan on the subject, which may reduce the time for obtaining the MR image with a relatively high image quality, thereby in turn reducing the time for main magnetic field homogenization.

In some embodiments, the preprocessing model may be constructed based on deep learning. In some embodiments, the preprocessing model may be constructed based on a neural network model. In some embodiments, the preprocessing model may be constructed based on a convolutional neural network (CNN), a self-encoding neural network based on multilayer neurons, a deep belief neural network, or the like. Exemplary CNN may include a fully convolutional neural network (FCN), a U-shape convolutional neural network (U-Net) (e.g., as shown in FIG. 7) that is an FCN-based deformation architecture, a generative adversarial neural network (GAN) (e.g., as shown in FIG. 8), a recurrent generative adversarial neural network, or the like. In some embodiments, the training process of the preprocessing model may include a supervised learning process, an unsupervised learning process, a semi-supervised learning process, or an active learning process.

In some embodiments, if the MR image is a magnetic field map, the ROI determination module 520 may obtain at least one ROI image by multiplying the at least one mask image by the MR image or the preprocessing MR image. In some embodiments, if the MR image is a magnitude image or a phase image, the ROI determination module 520 may generate a magnetic field map of the subject. The magnetic field map may include the at least one ROI. The ROI determination module 520 may obtain at least one ROI image by multiplying the at least one mask image by the magnetic field image. In some embodiments, each of the at least one ROI image may correspond to one of the at least one mask image and only present one or more of the at least one ROI of the subject.

In some embodiments, the ROI determination module 520 may select, based on the at least one ROI image, the portion of the main magnetic field on which the field homogenization operation is performed.

In some embodiments, some shim coils may be placed near or in the gap of the main magnet 201 of the scanner 110. The shim coils placed in different places may be configured to compensate for the inhomogeneity of different regions of the main magnetic field of the main magnet 201. In some embodiments, the ROI determination module 520 may determine a spatial location of the at least one ROI by analyzing the at least one ROI image. The ROI determination module 520 may select the portion of the main magnetic field to be homogenized based on the spatial location of the at least one ROI. For example, the ROI determination module 520 may determine, based on the spatial location of the at least one ROI, which of the shim coils is used to compensate for the inhomogeneity of the selected portion of the main magnetic field.

The homogenization module 530 may perform a magnetic field homogenization operation on the selected portion of the main magnetic field.

In some embodiments, the homogenization module 530 may perform the main magnetic field homogenization operation on the portion of the main magnetic field based on any existing magnetic field homogenization technique. For example, one or more homogenization parameters (e.g., a waveform of current applied to the shim coils) configured to generate offset electrical currents which pass through the shim coils to generate magnetic fields of the shim coils may be determined by analyzing the at least one ROI image. The magnetic fields of the shim coils may be configured to compensate for the inhomogeneity of the selected portion of the main magnetic field. The homogenization module 530 may perform the main magnetic field homogenization operation on the portion of the main magnetic field by causing the shim coils to operate based on the one or more homogenization parameters.

Merely by way of example, the homogenization module 530 may obtain the one or more homogenization parameters by performing harmonic analysis on the at least one ROI image. A regression analysis may be used to obtain a weight coefficient of a harmonic term of each order. In the regression analysis, the highest harmonic order may be set according to the highest order of the shim coils available in the scanner 110. The regression analysis may use a least squares algorithm to obtain the weight coefficients of each order of harmonics. The one or more homogenization parameters may be determined based on the weight coefficients of each order of harmonics.

A homogeneity degree of a region of the main magnetic field may indicate uniformity of a count of magnetic lines of force of the main magnetic field that pass through a unit area vertical to the region of the main magnetic field. In some embodiments, the portion of the main magnetic field may include at least one region each of which corresponds to one of the at least ROI. Each of the at least one region of the portion of the main magnetic field may correspond to a homogeneity threshold. The homogenization module 530 may perform the main magnetic field homogenization operation on the portion of the main magnetic field so that the homogeneity degree of each of the at least one region of the portion of the main magnetic field satisfies the corresponding homogeneity threshold. Under the homogenized main magnetic field, the image quality of the at least one ROI in the resulting image may be ensured.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of the processing device 140. As another example, each of the components of the processing device 140 may include a storage device. Additionally or alternatively, the components of the processing device 140 may share a common storage device.

Figure 6:
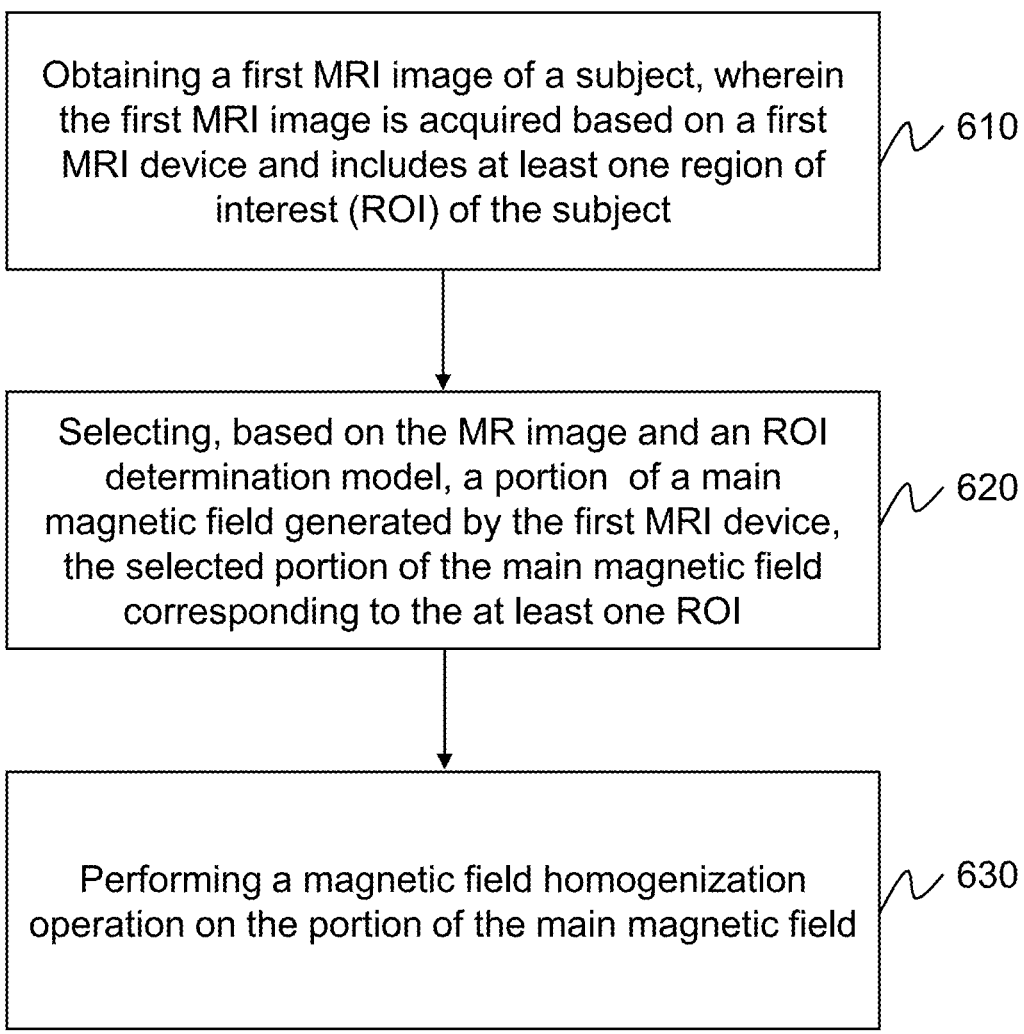
FIG. 6 is a flowchart illustrating an exemplary process for main magnetic field homogenization according to some embodiments of the present disclosure.

FIG. 6 is a flowchart illustrating an exemplary process for main magnetic field homogenization according to some embodiments of the present disclosure. In some embodiments, the process 600 may be implemented in the MRI system 100 illustrated in FIG. 1. For example, the process 600 may be stored in a storage device (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In some embodiments, before an MRI scan begins to perform on a subject using the scanner 110 of the MRI system 100 to generate one or more images of the subject, the processing device 140 may perform field homogenization on a portion of the main magnetic field generated by the scanner 110 based on the process 600.

In 610, the processing device 140 (e.g., the image obtaining module 510) may obtain an MR image of a subject. The MR image may be acquired by performing a scan on the subject using the scanner 110 of the MRI system 100 illustrated in FIG. 1. In some embodiments, the MR image may include at least one region of interest (ROI) of the subject. The at least one ROI may include tissue of the subject that a user (e.g., a doctor, an engineer, a technician, etc.) is interested in.

It should be noted that, in the present disclosure, an image, or a portion thereof (e.g., a region in the image) corresponding to a subject (e.g., tissue, an organ, a tumor, etc.) may be referred to as an image, or a portion of thereof (e.g., a region) of or including the subject, or the subject itself. For instance, a region in an image that corresponds to or represents an ROI of the subject may be referred to as an ROI of the subject or simply an ROI for brevity. As another example, an image of or including a breast of a subject may be referred to a breast image, or simply breast for brevity. For brevity, that a portion of an image corresponding to or representing an ROI of a subject is processed (e.g., extracted, segmented, etc.) may be described as that the ROI or the ROI of the subject is processed. For instance, that a portion of an image corresponding to a breast is segmented from the rest of the image may be described as that the breast is segmented from the image.

In some embodiments, MR data of the subject may be acquired based on the scan. The MR image may be obtained based on the acquired MR data of the subject. In some embodiments, the MR image may include a magnitude image or a phase image of the subject that is obtained by reconstructing the acquired MR data. In some embodiments, the MR image may include a magnetic field map of the subject. The magnetic field map may illustrate a main magnetic field distribution in the subject and offset phases in the magnetic field distribution due to field inhomogeneity of the main magnetic field.

In some embodiments, the scanner 110 may acquire the MR data of the subject using, for example, a gradient echo sequence, an echo planar imaging (EPI) sequence, a spiral acquisition sequence, etc. One or more images may be generated by image reconstruction using the MR data. The magnetic field map may be obtained by processing the one or more images. Alternatively, the magnetic field map may be obtained by processing the MR data using a mathematical model, such as a magnetic dipole model, an equivalent circuit model, an equivalent magnetic charge model, etc.

The time between two consecutive excitation radiofrequency (RF) pulses may refer to a repetition time (TR). When a pulse sequence is applied, in a single TR, one or more echoes may be generated. The time between the middle of the excitation RF pulse corresponding to the single TR and the peak of one of the one or more echoes generated in the single TR may be called an echo time (TE) of the echo. Merely by way of example, the scanner 110 may acquire MR data of the subject using a first three-dimensional (3D) gradient echo sequence and a second 3D gradient echo sequence. Parameters of the first and the second 3D gradient echo sequences may be the same except for the TE of the corresponding echo.

In some embodiments, a first image may be obtained based on the MR data acquired using the first 3D gradient echo sequence, and the second image may be obtained based on the MR data acquired using the second 3D gradient echo sequence. The magnetic field map may be obtained based on a difference between the first image and the second image. In some embodiments, the first image and the second image may be phase images. In some embodiments, for the first (or second) image, a magnitude template may be obtained based on the first (or second) image and a corresponding magnitude image to reduce or remove noise in the first (or second) image. In some embodiments, a phase unwrapping operation may be performed on the first and the second images.

In some embodiments, the difference LITE between the echo times of the first and the second 3D gradient echo sequences may be set so that the resultant MR data produced by the excitation of fat and water of the subject based on the first and the second 3D gradient echo sequences is in phase, and therefore the phase offset in the magnetic field map may be attributable to inhomogeneity in the main magnetic field. In other words, the phase evolution between the first and the second 3D gradient echo sequences is not affected by the phase difference of fat and water in the subject; instead, the phase evolution may be accumulated due to main magnetic field inhomogeneity.

In some embodiments, the MR image may have a relatively low image quality or a relatively high image quality. The image quality of an image may be measured by one or more image quality indexes, such as an image resolution, a noise level, a contrast ratio, a sharpness value, or the like, or any combination thereof. The image quality of two images may be compared by comparing the one or more image quality indexes. For example, image A may be regarded as having a higher image quality than image B if the image resolution of image A is higher than that of image B. Additionally or alternatively, image A may be regarded as having a higher image quality than image B if image A has a lower noise level (e.g., fewer artifacts) than image B.

Compared to an MR image with a relatively low image quality, an MR image with a relatively high image quality may include more anatomical details of the subject, or a portion thereof, which may make each of the at least one ROI in the MR image easier to be segmented or extracted. However, acquiring the MR image with a relatively high image quality by scanning the subject may take a longer time, which may make the time used to perform main magnetic field homogenization longer and make the main magnetic field homogenization inefficient.

In 620, the processing device 140 (e.g., the ROI determination module 520) may select, based on the MR image and an ROI determination model, a portion of a main magnetic field generated by the scanner 110 (e.g., the main magnet 201 in FIG. 2). The selected portion of the main magnetic field may correspond to the at least one ROI.

In some embodiments, the processing device 140 may generate, based on the ROI determination model and the MR image, at least one mask image. In some embodiments, a mask image may be a binary image. As used herein, a binary image may denote that the gray value of a pixel in the binary image may be "1" or "0." In some embodiments, the at least one mask image may indicate the at least one ROI. In some embodiments, each of the at least one mask image may indicate one or more of the at least one ROI. For example, one or more of the at least one ROI of the subject may be represented as pixels with the gray value of 1 in one of the at least one mask image, and the gray values of the rest pixels of the one of the at least one mask image may be equal to 0.

In some embodiments, the ROI determination model may be constructed based on deep learning. In some embodiments, the ROI determination model may be constructed based on a neural network model. In some embodiments, the ROI determination model may be constructed based on a convolutional neural network (CNN), a self-encoding neural network based on multilayer neurons, a deep belief neural network, or the like. Exemplary CNN may include a fully convolutional neural network (FCN), a U-shape convolutional neural network (U-Net) (e.g., as shown in FIG. 7) that is an FCN-based deformation architecture, a generative adversarial neural network (GAN) (e.g., as shown in FIG. 8), a recurrent generative adversarial neural network, or the like. In some embodiments, the training process of the ROI determination model may include a supervised learning process, an unsupervised learning process, a semi-supervised learning process, or an active learning process.

In some embodiments, the ROI determination model may be provided by the following operations. A plurality of groups of first training samples may be obtained. Each group of the plurality of groups of first training samples may include a first sample input image of a sample subject and at least one corresponding reference mask image. In some embodiments, one of the plurality of groups of first training samples may further include structure information of the same sample subject of other modalities, e.g., a CT image, a PET image, an X-ray image, an ultrasound image, a multi-modality image (e.g., an MRI-CT image, an PET-MRI image, a CT-PET image, etc.), or the like, or any combination thereof. In some embodiments, the first sample input images of the first training samples may include MR images of different subjects and may be acquired by a same MRI scanner or different MRI scanners. In some embodiments, at least one of the first sample input images of the first training samples may be obtained by processing (e.g., inverting, rotating, cutting, changing a pixel value of at least one pixel, etc.) a first sample input image in another group of the plurality of groups of the first training samples.

In some embodiments, for each group of the plurality of groups of first training samples, the first sample input image may include at least one reference ROI. The at least one corresponding reference mask image may indicate the at least one reference ROI of the first sample input image. A reference mask image may be a binary image. The at least one reference ROI of the first sample input image may be represented as pixels with the gray value of 1 in the at least one corresponding reference mask image. In some embodiments, a user may manually mark the at least one reference ROI in the first sample input image. The at least one corresponding reference mask image may be obtained based on the at least one marked reference ROI.

In some embodiments, the ROI determination model may be generated by training a first preliminary model using the plurality of groups of first training samples.

Merely by way of example, the first preliminary model may be initialized. For example, one or more parameters of the first preliminary model may be initialized. The ROI determination model may be generated by updating the initialized first preliminary model (e.g., updating the one or more initialized parameters of the first preliminary model) using a first iteration process including a plurality of iterations. In some embodiments, a stochastic gradient descent algorithm may be used to update the initialized first preliminary model through error back propagation. In some embodiments, each of the plurality of iterations of the first iteration process may include the following operations.

One of the plurality of groups of first training samples may be obtained. At least one intermediate mask image may be generated by inputting the first sample input image of the group of first training sample into a first intermediate model. The first intermediate model may be the initialized first preliminary model in the first iteration of the plurality of iterations of the first iteration process or a previously updated model generated in a previous iteration in the first iteration process. An intermediate mask image may indicate a candidate ROI. An intermediate mask image may be a binary image. A candidate ROI in the intermediate mask image may be represented as pixels with the gray value of 1, while the non-candidate ROI portion of the intermediate mask image may be represented as pixels with the gray value of 0 in the intermediate mask image.

In some embodiments, a value of a first cost function may be determined based on the at least one intermediate mask image and the at least one reference mask image of the group of first training samples. In some embodiments, the value of the first cost function may be determined based on a difference in at least one features between the at least one intermediate mask image and the at least one reference mask image of the group of first training samples. Exemplary features may include a size of an ROI (e.g., a candidate ROI in an intermediate mask image, or a corresponding reference ROI in the reference mask image), a location of an ROI (e.g., a candidate ROI in an intermediate mask image, or a corresponding reference ROI in the reference mask image), or the like, or a combination thereof.

In some embodiments, the first cost function may include a mean squared loss function, a Sigmoid activation function, a softmax loss function, a cross entropy loss function, a support vector machine (SVM) hinge loss function, a Smooth L1 loss function, or the like, or any combination thereof.

A determination may be made as to whether a first termination condition is satisfied. The first termination condition may relate to the value of the first cost function, a count of iterations of the first iteration process that have been performed, or the like, or a combination thereof. For example, the first termination condition may include at least one of a condition that the value of the first cost function may be within a first threshold range, or a condition that a count of iterations of the first iteration process that have been performed may be equal to a first count threshold. In response to determining that the first termination condition is not satisfied, an updated model may be generated by updating the first intermediate model, then a next iteration may be initiated. In response to determining that the first termination condition is satisfied, the first iteration process may be terminated. The updated model generated in the last iteration of the plurality of iterations of the first iteration process may be determined as the ROI determination model.

In some embodiments, before generating the at least one mask image, the processing device 140 may perform a preprocessing operation on the MR image. The processing device 140 may generate the at least one mask image based on the ROI determination model and the preprocessed MR image. In some embodiments, the preprocessing operation may include stretching, enlarging, shrinking, cutting, or the like, or any combination thereof.

In some embodiments, since the phase is defined within the range of $(-\pi, +\pi)$ when a phase image is generated, phase wrapping may occur in the phase image. If the MR image is a phase image, the preprocessing operation may include phase unwrapping. In some embodiments, the processing device 140 may perform phase unwrapping on the MR image based on a path tracking algorithm, a minimum norm algorithm, or the like, or any combination thereof. Exemplary path tracking algorithms may include a branch-cut algorithm.

In some embodiments, if the MR image is of a relatively low image quality, the preprocessing operation may include a process for improving the image quality of the MR image. The preprocessed MR image may have a higher image quality than the MR image. For example, the preprocessed MR image may be regarded as having a higher image quality than the MR image if the image resolution of the preprocessed MR image is higher than that of the MR image. Additionally or alternatively, the preprocessed MR image may be regarded as having a higher image quality than the MR image if the preprocessed MR image has a lower noise level (e.g., fewer artifacts) than the MR image. In some embodiments, the processing device 140 may perform the preprocessing for improving the image quality of the MR image based on interpolation, a machine learning model, or the like, or any combination thereof. For example, the processing device 140 may obtain the preprocessed MR image by processing the MR image based on a preprocessing model.

Compared to the MR image, the at least one ROI in the preprocessed MR image with a higher image quality may be easier to be differentiated from each other. Using the preprocessed MR image with a higher image quality to determine the at least one mask image may improve the accuracy for determining the at least one mask image. A process for obtaining an image with a relatively high image quality by scanning the subject may take a longer time than a process for obtaining an image with a relatively low image quality by scanning the subject. The preprocessed MR image with a higher image quality may be obtained by processing an MR image with a lower image quality, instead of by performing a high quality scan on the subject, which may reduce the time for obtaining the MR image with a relatively high image quality, thereby in turn reducing the time for main magnetic field homogenization.

In some embodiments, the preprocessing model may be constructed based on deep learning. In some embodiments, the preprocessing model may be constructed based on a neural network model. In some embodiments, the preprocessing model may be constructed based on a convolutional neural network (CNN), a self-encoding neural network based on multilayer neurons, a deep belief neural network, or the like. Exemplary CNN may include a fully convolutional neural network (FCN), a U-shape convolutional neural network (U-Net) (e.g., as shown in FIG. 7) that is an FCN-based deformation architecture, a generative adversarial neural network (GAN) (e.g., as shown in FIG. 8), a recurrent generative adversarial neural network, or the like. In some embodiments, the training process of the preprocessing model may include a supervised learning process, an unsupervised learning process, a semi-supervised learning process, or an active learning process.

In some embodiments, the preprocessing model may be provided by the following operations. A plurality of groups of second training samples may be obtained. In some embodiments, each group of the plurality of groups of second training samples may include a second sample input image and a corresponding reference image. The second sample input image may have a higher image quality than the corresponding reference image. In some embodiments, for at least one group of the second training samples, the second sample input image may be obtained by scanning a sample subject, and the corresponding reference image may be obtained by scanning the same sample subject using a same MRI scanners. In some embodiments, for at least one group of the second training samples, the reference image may be obtained by scanning a sample subject, and the corresponding second sample input image may be obtained by processing (e.g., downsampling) the reference image. In some embodiments, at least some of the plurality of groups of second training samples may be obtained by scanning different sample subjects using a same MRI scanner. In some embodiments, at least some of the plurality of groups of second training samples may be obtained by scanning different sample subjects using different MRI scanners.

In some embodiments, for at least one of the plurality of groups of the second training samples, the second sample input image may be obtained by processing (e.g., inverting, rotating, cutting, changing a pixel value of at least one pixel, etc.) a second sample input image in another group of the plurality of groups of the second training samples, and the corresponding reference image may be obtained by performing the same processing operation on the reference image in the other group of the plurality of groups of the second training samples.

In some embodiments, the preprocessing model may be generated by training a second preliminary model using the plurality of groups of second training samples.

Merely by way of example, the second preliminary model may be initialized. For example, one or more parameters of the second preliminary model may be initialized. The preprocessing model may be generated by updating the initialized second preliminary model (e.g., updating the one or more initialized parameters of the second preliminary model) using a second iteration process including a plurality of iterations. In some embodiments, a stochastic gradient descent algorithm may be used to update the initialized second preliminary model through error back propagation. In some embodiments, each of the plurality of iterations may include the following operations.

One of the plurality of groups of second training samples may be obtained. An intermediate image may be generated by inputting the second sample input image of the group of second training samples into a second intermediate model. The second intermediate model may be the initialized second preliminary model in the first iteration of the plurality of iterations of the second iteration process or a previously updated model generated in a previous iteration in the second iteration process.

In some embodiments, a value of a second cost function may be determined based on the intermediate image and the reference image of the group of second training samples. In some embodiments, the value of the second cost function may be determined based on a difference in at least one features. Exemplary features may include pixel values of pixels of an intermediate image, or a corresponding reference image, a first homogenization degree of the main magnetic field determined based on an intermediate image, a degree threshold, or the like, or a combination thereof.

In some embodiments, the second cost function may include a mean squared loss function, a Sigmoid activation function, a softmax loss function, a cross entropy loss function, a support vector machine (SVM) hinge loss function, a Smooth L1 loss function, or the like, or any combination thereof.

A determination may be made as to whether a second termination condition is satisfied. The second termination condition may relate to the value of the second cost function, a count of iterations of the second iteration process that have been performed, or the like, or a combination thereof. For example, the second termination condition may include at least one of a condition that the value of the second cost function may be within a second threshold range, and a condition that a count of iterations of the second iteration process that have been performed may be equal to a second count threshold. In response to determining that the second termination condition is not satisfied, an updated model may be generated by updating the second intermediate model, then a next iteration may be initiated. In response to determining that the second termination condition is satisfied, the second iteration process may be terminated. The updated model generated in the last iteration of the plurality of iterations of the second iteration process may be determined as the preprocessing model.

In some embodiments, the ROI determination model and/or the preprocessing model may be generated online or offline. In some embodiments, the ROI determination model and/or the preprocessing model may be generated and/or updated by the processing device 140. In some embodiments, the ROI determination model and/or the preprocessing model may be generated and/or updated by an external device and installed on the MRI system 100. In some embodiments, the ROI determination model and/or the preprocessing model may be updated periodically or from time to time.

In some embodiments, if the MR image is a magnetic field map, the processing device 140 may obtain at least one ROI image by multiplying the at least one mask image by the MR image or the preprocessing MR image. In some embodiments, if the MR image is a magnitude image or a phase image, the processing device 140 may generate a magnetic field map of the subject. Details related to generating the magnetic field map may be found elsewhere in the present disclosure (e.g., the description in connection with operation 610). The magnetic field map may include the at least one ROI. The processing device 140 may obtain at least one ROI image by multiplying the at least one mask image by the magnetic field image. In some embodiments, each of the at least one ROI image may correspond to one or more of the at least one mask image and only present one or more of the at least one ROI of the subject.

For example, the processing device 140 may obtain an MR image $I_1$ by scanning a subject using the scanner 110. $I_1$ may include an ROI $R_1$ of the subject and an ROI $R_2$ of the subject. The processing device 140 may obtain a preprocessed MR image $I_2$ by processing $I_1$ using the preprocessing model. $I_2$ may have a higher image quality than $I_1$. The processing device 140 may obtain, based on $I_2$ and the ROI determination model, 2 mask images, such as a mask image $M_1$ indicating the ROI $R_1$ and a mask image $M_2$ indicating the ROI $R_2$. The processing device 140 may obtain an ROI image $I_3$ by multiplying the mask image $M_1$ by a magnetic field image. The processing device 140 may obtain an ROI image $I_4$ by multiplying the mask image $M_2$ by the magnetic field image. $I_3$ may present only the ROI $R_1$. $I_4$ may present only the ROI $R_2$.

In some embodiments, the processing device 140 may select, based on the at least one ROI image, the portion of the main magnetic field on which the field homogenization operation is performed.

In some embodiments, some shim coils may be placed near or in the gap of the main magnet 201 of the scanner 110. The shim coils placed in different places may be configured to compensate for the inhomogeneity of different regions of the main magnetic field of the main magnet 201. In some embodiments, the processing device 140 may determine a spatial location of the at least one ROI by analyzing the at least one ROI image. The processing device 140 may select the portion of the main magnetic field to be homogenized based on the spatial location of the at least one ROI. For example, the processing device 140 may determine, based on the spatial location of the at least one ROI, which of the shim coils is used to compensate for the inhomogeneity of the selected portion of the main magnetic field.

In 630, the processing device 140 (e.g., the homogenization module 530) may perform a magnetic field homogenization operation on the selected portion of the main magnetic field.

In some embodiments, the processing device 140 may perform the main magnetic field homogenization operation on the portion of the main magnetic field based on any existing magnetic field homogenization technique. For example, one or more homogenization parameters (e.g., a waveform of current applied to the shim coils) configured to generate offset electrical currents which pass through the shim coils to generate magnetic fields of the shim coils may be determined by analyzing the at least one ROI image. The magnetic fields of the shim coils may be configured to compensate for the inhomogeneity of the selected portion of the main magnetic field. The processing device 140 may perform the main magnetic field homogenization operation on the portion of the main magnetic field by causing the shim coils to operate based on the one or more homogenization parameters.

Merely by way of example, the processing device 140 may obtain the one or more homogenization parameters by performing harmonic analysis on the at least one ROI image. A regression analysis may be used to obtain a weight coefficient of a harmonic term of each order. In the regression analysis, the highest harmonic order may be set according to the highest order of the shim coils available in the scanner 110. The regression analysis may use a least squares algorithm to obtain the weight coefficients of each order of harmonics. The one or more homogenization parameters may be determined based on the weight coefficients of each order of harmonics.

A homogeneity degree of a region of the main magnetic field may indicate uniformity of a count of magnetic lines of force of the main magnetic field that pass through a unit area vertical to the region of the main magnetic field. In some embodiments, the portion of the main magnetic field may include at least one region each of which corresponds to one of the at least ROI. Each of the at least one region of the portion of the main magnetic field may correspond to a homogeneity threshold. The processing device 140 may perform the main magnetic field homogenization operation on the portion of the main magnetic field so that the homogeneity degree of each of the at least one region of the portion of the main magnetic field satisfies the corresponding homogeneity threshold. Under the homogenized main magnetic field, the image quality of the at least one ROI in the resulting image may be ensured.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the preprocessing model provided in the present disclosure may be used to generate an image with a relatively high image quality based on an image with a relatively low image quality. The image with a relatively high image quality and/or the image with a relatively low image quality may include a single modality image (e.g., an MR image, a CT image, a PET image, an X-ray image, etc.) or a multi-modality image (e.g., an MRI-CT image, a PET-MRI image, a PET-CT image, etc.). As another example, the ROI determination model provided in the present disclosure may be used to segment one or more ROIs from an image. The image may include a single modality image (e.g., an MR image, a CT image, a PET image, an X-ray image, etc.) or a multi-modality image (e.g., an MRI-CT image, a PET-MRI image, a PET-CT image, etc.).

FIG. 7 is a schematic diagram illustrating an exemplary U-shape convolutional neural network (U-Net) architecture according to some embodiments of the present disclosure. As shown in FIG. 7, gray boxes (e.g., a box 710 in FIG. 7) refer to multi-channel feature map. White boxes (e.g., a box 720 in FIG. 7) refer to copied feature maps. Different arrows refer to different operations. For example, an arrow 730 refers to an operation of convolution and an activation function. An arrow 740 refers to an up-sampling operation. An arrow 750 refers to a downsampling operation. An arrow 760 refers to an operation of transforming connection. An arrow 770 refers to a convolution operation.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 8 is a schematic diagram illustrating an exemplary generative adversarial neural network (GAN) architecture according to some embodiments of the present disclosure. As shown in FIG. 8, the GAN may include a generator configured to generate a predicted image based on an input image and a discriminator configured to discriminate the predicted image and a true image relative to the predicted image.

For example, the ROI determination model may be a GAN that is obtained based on a first iteration process including a plurality of iterations of the training process of the ROI determination model illustrated in FIG. 6. In one of the plurality of iterations of the first iteration process, a first sample input image and random noise may be input into the generator. The generator may output an intermediate mask image (e.g., a predicted image). The intermediate mask image and a reference mask image (e.g., a true image relative to the intermediate mask image) may be input into the discriminator. The discriminator may discriminate the intermediate mask image and the reference mask image. The discriminator may determine the intermediate mask image as false and determine the reference mask image as true. The discriminator may output an image loss (e.g., a value of a first cost function) between the intermediate mask image and the reference mask image. After the GAN is trained, the generator of the GAN may be used to generate a mask image based on an input image.

As another example, the preprocessing model may be a GAN that is obtained based on a second iteration process including a plurality of iterations of the training process of the preprocessing model illustrated in FIG. 6. In one of the plurality of iterations of the second iteration process, a second sample input image and random noise may be input into the generator. The generator may output an intermediate image (e.g., a predicted image). The intermediate image and a reference image (e.g., a true image relative to the intermediate image) may be input into the discriminator. The discriminator may discriminate the intermediate image and the reference image. The discriminator may determine the intermediate image as false and determine the reference image as true. The discriminator may output an image loss (e.g., a value of a second cost function) between the intermediate image and the reference image. After the GAN is trained, the generator of the GAN may be used to generate an image with relatively high image quality based on an image with relatively low image quality.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 9:
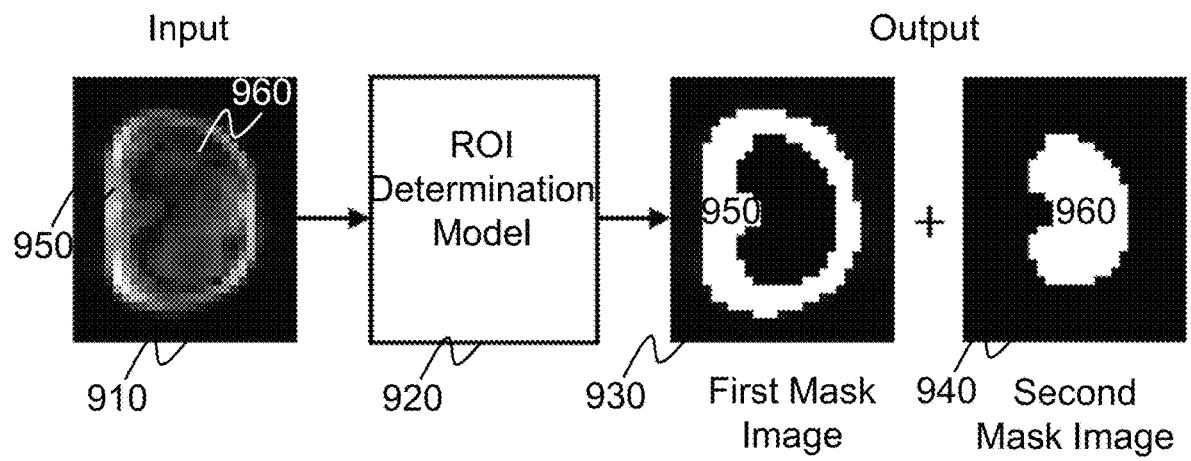
FIG. 9 is a schematic diagram illustrating an exemplary process for determining at least one mask image based on a region of interest (ROI) determination model according to some embodiments in the present disclosure.

FIG. 9 is a schematic diagram illustrating an exemplary process for determining at least one mask image based on the ROI determination model according to some embodiments in the present disclosure. As shown in FIG. 9, image 910 is an MR image (e.g., an MR image obtained by image reconstruction based on MR data acquired by a scan, or a preprocessed MR image obtained by preprocessing such an MR image). Image 910 includes ROI 950 and ROI 960 of a subject. Image 910 was input into the ROI determination model 920. The ROI determination model 920 output a first mask image 930 and a second mask image 940. The first mask image 930 is a binary image in which ROI 950 is represented as white (e.g., gray values of pixels in ROI 950 equal to 1), while the remaining (non-ROI) portion is represented as black (e.g., gray values of pixels equal to 0). The second mask image 940 is a binary image in which ROI 960 is represented as white (e.g., gray values of pixels in ROI 960 equal to 1), while the remaining (non-ROI) portion is represented as black (e.g., gray values of pixels equal to 0).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
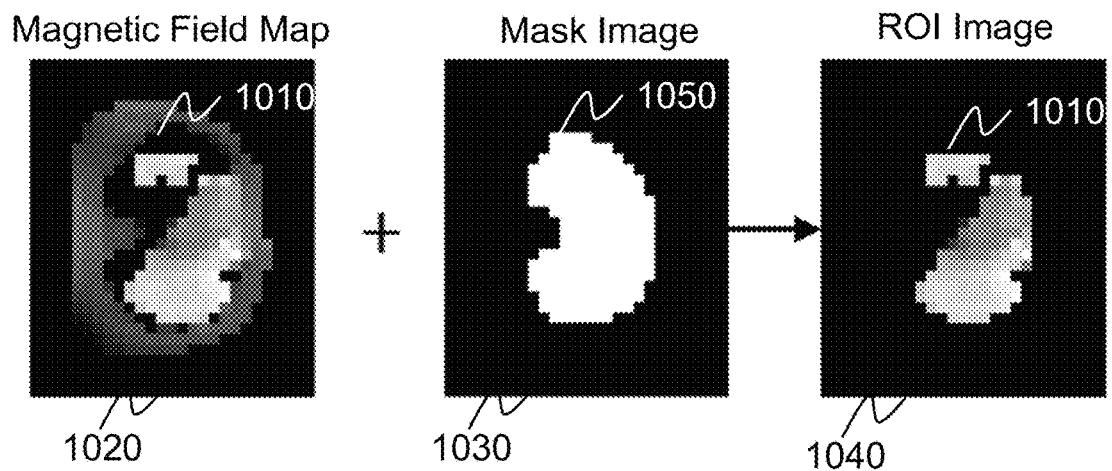
FIG. 10 is a schematic diagram illustrating an exemplary process for obtaining an ROI image based on at least one mask image according to some embodiments in the present disclosure.

FIG. 10 is a schematic diagram illustrating an exemplary process for obtaining an ROI image based on at least one mask image according to some embodiments in the present disclosure. As shown in FIG. 10, a magnetic field map 1020 includes ROI 1010 of a subject. A mask image 1030 is a binary image in which a region 1050 corresponding to ROI 1010 is represented as white (e.g., gray values of pixels in region 1050 equal to 1), while the remaining (non-ROI) portion is represented as black (e.g., gray values of pixels equal to 0). The mask image 1030 was applied to the magnetic field map 1020 to extract the ROI 1010 from the magnetic field map 1020. The extraction result is shown as ROI image 1040 in FIG. 10.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for magnetic resonance imaging (MRI), comprising:
   at least one storage device storing a set of instructions; and
   at least one processor in communication with the at least one storage device, when executing the stored set of instructions, the at least one processor causes the system to perform operations including:
   obtaining a magnetic resonance (MR) image of a subject, wherein the MR image is acquired based on a first MRI device and includes at least one region of interest (ROI) of the subject;
   selecting, based on the MR image and an ROI determination model, a portion of a main magnetic field generated by the first MRI device, the selected portion of the main magnetic field corresponding to the at least one ROI; and
   performing a magnetic field homogenization operation on the selected portion of the main magnetic field.

2. The system of claim 1, wherein the selecting, based on the MR image and the ROI determination model, a portion of the main magnetic field generated by the first MRI device includes:
   generating, based on the ROI determination model and the MR image, at least one mask image, one of the at least one mask image corresponding to one or more of the at least one ROI;
   obtaining a magnetic field map of the subject, the magnetic field map including the at least one ROI;
   obtaining at least one ROI image by segmenting the at least one ROI from the magnetic field map based on the at least one mask image; and
   selecting, based on the at least one ROI image, the portion of the main magnetic field on which the field homogenization operation is performed.

3. The system of claim 2, wherein the ROI determination model is obtained according to a first training process including:
   obtaining a plurality of groups of first training samples; and
   generating the ROI determination model by training a first preliminary model using the plurality of groups of first training samples.

4. The system of claim 3, wherein the generating the ROI determination model by training the first preliminary model using the plurality of groups of first training samples includes:
   initializing the first preliminary model;
   generating the ROI determination model by updating the initialized first preliminary model using a first iteration process including a plurality of iterations, each of the plurality of iterations of the first iteration process including:
      obtaining one of the plurality of groups of first training samples that includes a first sample input image and at least one corresponding reference mask image relating to at least one reference ROI of the first sample input image;
      generating at least one intermediate mask image by inputting the first sample input image of the group of first training sample into a first intermediate model, the first intermediate model being the initialized first preliminary model in a first iteration of the plurality of iterations of the first iteration process or a previously updated model generated in a previous iteration in the first iteration process, the intermediate mask image including at least one candidate ROI of the first sample input image;
      determining a value of a first cost function based on the at least one intermediate mask image and the at least one reference mask image of the group of first training sample;
      determining whether a first termination condition is satisfied;
      in response to determining that the first termination condition is not satisfied,
         generating an updated model by updating the first intermediate model; and
         initiating a next iteration; and
   determining the updated model generated in a last iteration of the plurality of iterations of the first iteration process as the ROI determination model.

5. The system of claim 4, wherein the value of the first cost function is determined based on at least one of a difference between a size of the at least one candidate ROI in the at least one intermediate mask image and a size of the at least one reference ROI in the at least one reference mask image, or a difference between a location of the at least one candidate ROI in the at least one intermediate mask image and a location of the at least one reference ROI in the at least one reference mask image.

6. The system of claim 4, wherein the first termination condition relates to at least one of the value of the first cost function or a count of iterations of the first iteration process that have been performed.

7. The system of claim 2, wherein the generating, based on the ROI determination model and the MR image, the at least one mask image includes:

preprocessing the MR image; and generating the at least one mask image based on the ROI determination model and the preprocessed MR image.

8. The system of claim 7, wherein the preprocessing the MR image includes at least one of the following operations:

performing a phase unwrapping operation on the MR image; or preprocessing the MR image based on a preprocessing model, the preprocessed MR image having a higher image quality than the MR image.

9. The system of claim 8, wherein the image quality relates to an image resolution.

10. The system of claim 8, wherein the preprocessing model is obtained according to a second training process including:

obtaining a plurality of groups of second training samples; and generating the preprocessing model by training a second preliminary model using the plurality of groups of second training samples.

11. The system of claim 10, wherein the generating the preprocessing model by training the second preliminary model using the plurality of groups of second training samples includes:

initializing the second preliminary model;

generating the preprocessing model by updating the initialized second preliminary model using a second iteration process including a plurality of iterations, each of the plurality of iterations of the second iteration process including:

obtaining one of the plurality of groups of second training samples that includes a second sample input image and a corresponding reference image, the second sample input image having a higher image quality than the corresponding reference image;

generating an intermediate image by inputting the second sample input image of the group of first training sample into a second intermediate model, the second intermediate model being the initialized second preliminary model in a first iteration of the plurality of iterations of the second iteration process or a previously updated model generated in a previous iteration in the second iteration process;

determining a value of a second cost function based on the intermediate image and the reference image of the group of second training sample;

determining whether a second termination condition is satisfied;

in response to determining that the second termination condition is not satisfied, generating an updated model by updating the second intermediate model; and initiating a next iteration; and determining the updated model generated in a last iteration of the plurality of iterations of the second iteration process as the preprocessing model.

12. The system of claim 11, wherein the second sample input image and the corresponding reference image of at least one of the plurality of groups of second training samples are obtained by scanning a sample subject using a second MRI device.

13. The system of claim 11, wherein the reference image of at least one of the plurality of groups of second training samples is obtained by scanning a sample subject using a third MRI device, and the corresponding second sample input image of the at least one of the plurality of groups of second training samples is obtained by processing the reference image.

14. The system of claim 11, wherein the value of the second cost function is determined based on at least one of a difference between pixel values of pixels of the intermediate image and pixel values of pixels of the reference image, or a difference between a homogenization degree of the main magnetic field determined based on the intermediate image and a degree threshold.

15. The system of claim 11, wherein the second termination condition relates to the value of the second cost function, or a count of iterations of the second iteration process that have been performed.

16. The system of claim 8, wherein the preprocessing model is constructed based on at least one of a U-shape network (U-Net), a generative adversarial network (GAN), or a recurrent generative adversarial network.

17. The system of claim 1, wherein the ROI determination model is constructed based on a U-shape network (U-Net).

18. The system of claim 1, wherein the magnetic field homogenization operation is performed on the selected region of the main magnetic field based on at least one homogeneity threshold each of which corresponds to one of the at least one ROI.

19. A system for magnetic resonance imaging (MRI), comprising:

at least one storage device storing a set of instructions; and at least one processor in communication with the at least one storage device, when executing the stored set of instructions, the at least one processor causes the system to perform operations including:

obtaining a magnetic resonance (MR) image of a subject, wherein the MR image includes at least one region of interest (ROI) of the subject;

preprocessing the MR image based on a preprocessing model, the preprocessed MR image having a higher image quality than the MR image;

generating at least one mask image based on an ROI determination model and the preprocessed MR image, one of the at least one mask image corresponding to one or more of the at least one ROI; and obtaining at least one ROI image based on the at least one mask image.

20. A method for magnetic resonance imaging (MRI) implemented on a machine having at least one processor and at least one storage device, comprising:

obtaining a magnetic resonance (MR) image of a subject, wherein the MR image is acquired based on a first MRI device and includes at least one region of interest (ROI) of the subject;

selecting, based on the MR image and an ROI determination model, a portion of a main magnetic field generated by the first MRI device, the selected portion of the main magnetic field corresponding to the at least one ROI; and
performing a magnetic field homogenization operation on the selected portion of the main magnetic field.

* * * * *